US012620476B2

(12) United States Patent
Sadeghi et al.

(10) Patent No.: US 12,620,476 B2
(45) Date of Patent: May 5, 2026

(54) CARDIAC IMAGE WORKFLOW INTERPRETATION TIME PREDICTION

(71) Applicant: KONINKLIJKE PHILIPS N.V., Eindhoven (NL)

(72) Inventors: Ali Sadeghi, Melrose, MA (US); Lucas de Melo Oliveira, Wilmington, MA (US); Deyu Sun, Chicago, IL (US); Hua Xie, Cambridge, MA (US); Claudia Errico, Medford, MA (US); Jochen Kruecker, Andover, MA (US)

(73) Assignee: KONINKLIJKE PHILIPS N.V., Eindhoven (NL)

( * ) Notice: Subject to any disclaimer, the term of this patent is extended or adjusted under 35 U.S.C. 154(b) by 222 days.

(21) Appl. No.: 18/274,242

(22) PCT Filed: Jan. 18, 2022

(86) PCT No.: PCT/EP2022/050928
§ 371 (c)(1),
(2) Date: Jul. 26, 2023

(87) PCT Pub. No.: WO2022/161808
PCT Pub. Date: Aug. 4, 2022

(65) Prior Publication Data
US 2024/0105313 A1 Mar. 28, 2024

Related U.S. Application Data

(60) Provisional application No. 63/141,995, filed on Jan. 27, 2021.

(51) Int. Cl.
*G16H 30/40* (2018.01)
*G16H 40/20* (2018.01)

(52) U.S. Cl.
CPC ............. *G16H 30/40* (2018.01); *G16H 40/20* (2018.01)

(58) Field of Classification Search
CPC ............................. G16H 30/40; G16H 40/20
(Continued)

(56) References Cited

U.S. PATENT DOCUMENTS 6,401,055 B1 * 6/2002 Petta ...................... G06Q 10/02
600/407
8,249,892 B2 * 8/2012 Reiner ................... G16H 10/60
382/128
(Continued)

FOREIGN PATENT DOCUMENTS

WO WO-2022161808 A1 * 8/2022 ............. G16H 40/20

OTHER PUBLICATIONS

International Search Report and Written Opinion for PCT/EP2022/050928; Mailing date: May 12, 2022, 11 pages.
(Continued)

*Primary Examiner* — Michael Tomaszewski

(57) ABSTRACT

A method predicts an interpretation time for a medical image examination of a subject comprising one or more medical images. A plurality of data inputs is obtained, where the data inputs are associated with the medical image examination or the subject of the medical image examination, and the data points represent parameters affecting the interpretation time. The plurality of data inputs are input to a trained artificial intelligence algorithm, wherein the algorithm automatically provides a predicted interpretation time based on said plurality of data inputs. The predicted interpretation time is output to a clinical management system. A clinical management system incorporating the aforementioned method and a computer program product encoded with the aforementioned method are also provided.

17 Claims, 6 Drawing Sheets

(58) Field of Classification Search
USPC .......................................................... 705/2–3
See application file for complete search history.

(56) References Cited

U.S. PATENT DOCUMENTS

| | | | | |
|---|---|---|---|---|
| 11,694,792 | B2 * | 7/2023 | Kshirsagar | G06T 7/0012 |
| | | | | 382/128 |
| 12,119,107 | B2 * | 10/2024 | Kshirsagar | G16H 30/40 |
| 2005/0002483 | A1 * | 1/2005 | Wilcox, Jr. | G16H 30/20 |
| | | | | 705/2 |
| 2008/0312963 | A1 * | 12/2008 | Reiner | G06Q 10/06398 |
| | | | | 705/7.42 |
| 2011/0218815 | A1 * | 9/2011 | Reiner | G16H 10/60 |
| | | | | 705/2 |
| 2015/0052058 | A1 * | 2/2015 | McCown | G06Q 10/063114 |
| | | | | 705/2 |
| 2018/0060512 | A1 * | 3/2018 | Sorenson | G06Q 10/06398 |
| 2018/0101645 | A1 * | 4/2018 | Sorenson | G06V 30/19167 |
| 2021/0098120 | A1 * | 4/2021 | Kshirsagar | G06Q 10/1097 |
| 2022/0004863 | A1 * | 1/2022 | Park | G06N 3/09 |
| 2023/0044416 | A1 * | 2/2023 | Sadeghi | H01M 10/058 |
| 2024/0021297 | A1 * | 1/2024 | Kshirsagar | G16H 50/30 |
| 2024/0105313 | A1 * | 3/2024 | Sadeghi | G16H 30/40 |
| 2025/0104865 | A1 * | 3/2025 | Yatsuo | G16H 40/40 |

OTHER PUBLICATIONS

Syed, A. B. et al., "Artificial Intelligence in Radiology: Current Technology and Future Directions", Semin Musculoskelet Radiol., 2018, vol. 22, No. 5, pp. 540-545.

Pham, T. -P. et al., "Predicting Workflow Task Execution Time in the Cloud Using a Two-Stage Machine Learning Approach", IEEE Transactions on Cloud Computing, 2020, vol. 8, No. 1, pp. 256-268.

Lingitz, L. et al., "Lead time prediction using machine learning algorithms: A case study by a semiconductor manufacturer", Procedia CIRP, 2018, vol. 72, pp. 1051-1056.

Dey, D. et al., "Artificial Intelligence in Cardiovascular Imaging", J Am Coll Cardiol., 2019, vol. 73, No. 11, pp. 1317-1335.

Stepaniak, P.S. et al., "Modeling Procedure and Surgical Times for Current Procedural Terminology-Anesthesia Surgeon Combinations and Evaluation in Terms of Case-Duration Prediction and Operating Room Efficiency: A Multicenter Study", Anesth Analg., 2009, vol. 109, No. 4, pp. 1232-1245.

Li, Q. et al., "Echo Lab Continuous Improvement Impacting cardiac care delivery", Philips, 2017, 6 pages.

Baltruschat, I.M. et al., "Smart Chest X-ray Worklist Prioritization using Artificial Intelligence: A Clinical Workflow Simulation", arXiv:2001.08625v2, 2020, 14 pages.

Nagueh, S. et al., "Recommendations for the Evaluation of Left Ventricular Diastolic Function by Echocardiography: An Update from the American Society of Echocardiography and the European Association of Cardiovascular Imaging", Eur Heart J Cardiovasc Imaging, 2016, vol. 17, No. 12, pp. 1321-1360.

Botvinick, M. et al., "Reinforcement Learning, Fast and Slow", Trends in cognitive sciences, 2019, vol. 23, Issue 5, pp. 408-422.

Powell, W.B., "Perspectives of approximate dynamic programming", Annals of Operations Research, 2016, vol. 241, pp. 319-356.

* cited by examiner

401

| Patient Name | Age | Gender | Radiologist | Estimated Interpretation Time |
|---|---|---|---|---|
| Story, Susan | 19Y 5M | F | Evans David | 6min |
| Dunning, Ralph | 81Y 8M | M | Blankenship Nathaniel | 13min |
| Holbert, Kathleen | 79Y 4M | F | Blankenship Nathaniel | 18min |
| Brown, Lois | 78Y 6M | M | Keaton Robert | 19min |
| Moore, Emily | 14Y 4M | F | Evans David | 21min |
| Harris, Benjamin | 60Y 3M | M | Morris Lawerence | 22min |
| Taylor, James | 73Y 2M | M | Morris Lawerence | 22min |
| Wright, Chloe | 20Y 6M | F | Blankenship Nathaniel | 13min |

| Disease Type | Age | Gender | Estimated Interpretation Time |
|---|---|---|---|
| Mitral Valve Prolapse | 23Y 2M | F | 5min |
| Mitral Valve Stenosis | 32Y 0M | M | 22min |
| Left Ventrical Hypertrophy | 46Y 8M | F | 25min |
| Mitral Valve Regurgitation | 36Y 4M | F | 14min |
| Hypertrophy Cardiomyopathy | 61Y 3M | M | 21min |
| Atrial Fibrillation | 55Y 1M | F | 28min |
| Amyloidosis | 73Y 1M | M | 45min |
| Systolic Dysfunction | 21Y 7M | M | 12min |

| |
|---|
| Obtain Available Cardioloist Time |
| _701_ |

| |
|---|
| Obtain Predicted Interpretation Time For Each Pending Examination |
| _702_ |

| |
|---|
| Select Combination Of Examinations With Cumultive Predicted Interpretation Time Less Than Available Cardiologist's Time |
| _703_ |

| |
|---|
| Provide List Of Selected Examinations To Cardiologist |
| _704_ |

Search
_801_

Display                    _241_

CARDIAC IMAGE WORKFLOW INTERPRETATION TIME PREDICTION

CROSS-REFERENCE TO PRIOR APPLICATIONS

This application is the U.S. National Phase application under 35 U.S.C. § 371 of International Application No. PCT/EP2022/050928, filed on Jan. 18, 2022, which claims the benefit of U.S. Provisional Patent Application No. 63/141,995, filed on Jan. 27, 2021. These applications are hereby incorporated by reference herein.

FIELD OF THE INVENTION

The invention relates to the field of medical image interpretation workflow and more particularly to predicting medical image interpretation times to enhance workflow, productivity and resource planning.

BACKGROUND

Due to an increased cardiac imaging workflow and shortage of medical experts worldwide, Echocardiogram or Echo Lab directors are under pressure to improve efficiency. Clinical management systems, such as Intellispace Cardiovascular (ISCV) from Koninklijke Philips N.V. of Eindhoven, the Netherlands, facilitate workflow management of cardiac imaging by managing images, information, and workflow and providing workflow visibility to cardiologists, lab directors, and other medical personnel at multiple locations and in multiple data configurations.

An integral part of improving cardiac imaging workflow efficiency is obtaining quick turnaround times (TOT) for image interpretation, without compromising the quality of health outcomes. Currently, in most hospital settings, due to variations of clinical situations for different patients, cardiologists do not know what interpretation time to expect in advance for each image interpretation. The interpretation time can vary from 5 minutes to 50 minutes depending on the disease type, clinical features, and level of complexity of the individual image interpretation. Interpretation time uncertainty can reduce workflow efficiency.

The assignment of cardiologists to exams depends on the hospital workflow. Often hospitals have attending cardiologists, assigned by day of the week, for example. Many cardiologists process their examination worklists following the first-in first-out principle. As exams arrive for image interpretation, cardiologists pick them to read. If there is any urgency, the sonographer may call the attending cardiologist to point out a specific exam that needs to be completed with higher priority. It is also common for a cardiologist to select less complex exams or exams that the cardiologist feels more confident with to read first. Neither of these workflows or resource planning methods is optimized for productivity or health outcome quality, given the uncertainty of about the time needed for interpretation of each exam. It is also common for image interpretation to be provided on a service level agreement, where final imaging reports must be completed within a specified TOT. Managing the contracted TOT is difficult when the interpretation time is unknown.

There are existing workflow tools such as the worklist orchestrator management solution provided by Carestream HCIS (as part of the Clinical Collaboration Platform's architecture) that provide adaptive worklist prioritization to balance the radiologist's workload and maximize the probability that an exam be read within its service level agreement. The prioritization feature is specifically designed to show radiologists the time remaining before breaching the service level agreement.

SUMMARY

The inventors of the present invention have realized that accurately predicting interpretation time for medical images and making these predictions available to medical personnel can improve efficiency and enhance workflow management. Accordingly, the present invention provides a method, system, and program product for predicting interpretation time for medical images and providing these predictions to medical personnel through a clinical management system for use in workflow management. With the ratio of examination volume to the number of available cardiologists increasing, reading efficiency and the time spent by cardiologists for image interpretation to provide the final report plays a pivotal role in enabling the hospital to potentially accept more patients. Therefore, having prior knowledge about the interpretation time gives flexibility to the cardiologist to manage their time more efficiently and contribute to quicker TOT, enabling the hospital to potentially take more patients. Also, prior knowledge of interpretation time allows the hospital and the cardiologist to manage the workflow to complete the interpretation for each exam within a timeframe that supports the quality of health outcomes.

According to a first aspect of the present invention, a method is provided for predicting an interpretation time for a medical image examination of a subject comprising one or more medical images. The method starts by obtaining a plurality of data inputs, where the data inputs are associated with the medical image examination and/or the subject of said medical image examination, and the data points represent parameters affecting the interpretation time. The plurality of data inputs are input to a trained artificial intelligence algorithm, wherein the algorithm automatically provides a predicted interpretation time based on the plurality of data inputs. The predicted interpretation time is output to a clinical management system.

According to one embodiment of the invention the artificial intelligence algorithm further provides a confidence level for the predicted interpretation time.

According to one embodiment of the invention the artificial intelligence algorithm ranks the predicted interpretation time relative to predicted interpretation times for other pending medical image examinations and highlights the longest predicted interpretation time.

According to one embodiment of the invention, the plurality of data inputs comprises: at least one of body mass index of the subject of the medical image examination and patient age, at least one of type of medical image study, previous image modalities available, disease type, history of diastolic dysfunction, presence of atrial fibrillation, and presence of coronary artery disease, and at least one of type of imaging modality, number of archived images or loops, and exam type.

According to one embodiment of the invention, the plurality of data inputs comprises each of: body mass index of the subject of the medical image examination, type of medical image study, patient age, patient gender, previous image modalities available, disease type, history of diastolic dysfunction, presence of atrial fibrillation, presence of coronary artery disease, type of imaging modality, number of archived images or loops, sonographer's notes, and exam type.

According to one embodiment of the invention, the artificial intelligence algorithm is a regression-based algorithm and prior to the step of obtaining a plurality of data inputs, the artificial intelligence algorithm obtains data inputs and actual interpretation times for a plurality of use cases and trains the regression-based algorithm to map a state defined by the data inputs to a predicted interpretation time using a reinforcement learning approach.

According to one embodiment of the invention, the training step uses a policy of minimizing a reward function, the reward function being the absolute value of the difference between the predicted interpretation time and the actual interpretation time for each use case.

According to one embodiment of the invention, the reward function is updated using Bellman's equation for reinforcement learning.

According to one embodiment of the invention, the artificial intelligence algorithm obtains actual interpretation time for the medical image examination; wherein the artificial intelligence algorithm uses the actual interpretation time and the plurality of data inputs for reinforcement learning.

According to another aspect of the present invention, a clinical management system configured to predict an interpretation time for a medical image study is provided. The clinical management system comprises a processor operably connected to a memory, the memory having encoded thereon machine-readable program code, which when executed by the processor, causes the processor to: obtain a plurality of data inputs associated with said medical image study or the subject of said medical image study; input the plurality of data inputs to a trained artificial intelligence algorithm, wherein the algorithm automatically provides a predicted interpretation time based on said plurality of data inputs; and provide said predicted interpretation time to a clinical management system.

According to one embodiment, the predicted interpretation time is presented in a table of medical imaging examinations awaiting interpretation.

According to one embodiment, the clinical management system obtains a user's available time for image interpretation, selects a combination of examinations waiting for interpretation, and presents a list of the selected combination of examinations to the user.

According to another aspect of the present invention, a computer program product is provided for predicting interpretation time for an imaging examination. The computer program product comprises a machine-readable storage media having encoded thereon program code, comprising: program code for obtaining a plurality of data inputs, the data inputs being associated with the medical image examination or the subject of the medical image examination, wherein the data points represent parameters affecting the interpretation time; program code for inputting the plurality of data inputs to a trained artificial intelligence algorithm, wherein the algorithm automatically provides a predicted interpretation time based on the plurality of data inputs; and program code for providing the predicted interpretation time to a clinical management system.

The invention may be realized by software stored on a memory and executed by a processor operably connected to the memory. The predicted interpretation time may be presented on a display operably connected to the processor in a variety of data formats through any known connection method using any known communication protocol.

The term "processor", when used herein shall mean a single processor or a plurality of processors that may be interconnected through hardwiring or wireless connection or may be in communication through a network. The processors may be single core or multi-core processors.

The term "memory", when used herein, shall mean a machine-readable medium that is either integral with the processor, such as in a workstation or general-purpose computer, or external to processor, such as an external hard drive, cloud storage, or a removable memory device. The medium can be an electronic, magnetic, optical, electromagnetic, infrared, or semiconductor system (or apparatus or device). Examples of a computer-readable medium include a semiconductor or solid-state memory, magnetic tape, a removable computer diskette, a random access memory (RAM), a read-only memory (ROM), a rigid magnetic disk, and an optical disk. Current examples of optical disks include compact disk-read only memory (CD-ROM), compact disk-read/write (CD-RAY) and DVD.

The term "display", when used herein, shall mean a human viewable computer interface for presenting image data or streams with or without additional images or data as stationary or moving pictures connected to the processor via video graphics array (VGA), digital visual interface (DVI), high-definition multimedia interface (HDMI), low-voltage differential signaling (LVDS) or other proprietary connectors and signals. Examples of currently used displays include liquid crystal displays, light emitting diode displays, plasma displays.

The term "and/or", when used herein, shall mean only the first possibility, only the second possibility, only the third possibility, and so forth as well as any combination of the listed possibilities. For example, the phrase A, B, and/or C can be any of: only A, only B, only C, A and B, A and C, B and C, or A, B, and C.

The term "image interpretation", when used herein, shall mean visual review, image manipulation, spatial measurement, temporal measurement, and/or the use of any other imaging tool for identifying characteristics from image data for the purpose of determining medically relevant conditions or making diagnoses.

The term "clinical management system", when used herein shall mean a computer-based system for managing clinical processes and data to provide process visibility and workflow efficiency, such as Intellispace Cardiovascular (ISCV).

The term "artificial intelligence algorithm", when used herein shall mean computer code that can take data (typically in real-time) from multiple sources and take actions (such as making predictions) based on the data and principles, such as minimizing error, based on self-learning, such as reinforcement learning.

The terms "examination variables" and "state variables" when used herein shall mean values that are examination specific, such as attributed of a patient, medical history of a patient, or specific attributed of the examination process.

BRIEF DESCRIPTION OF THE DRAWINGS

The features and advantages of the invention will be more clearly understood from the following detailed description of the preferred embodiments when read in connection with the accompanying drawing. Included in the drawing are the following figures:

FIG. 4 is a view of a display of a clinical management system showing predicted image examination interpretation times in a first format according to an embodiment of the invention;

FIG. 5 is a view of a display of a clinical management system showing predicted image examination interpretation times in a second format according to an embodiment of the invention;

DETAILED DESCRIPTION

Figure 1:
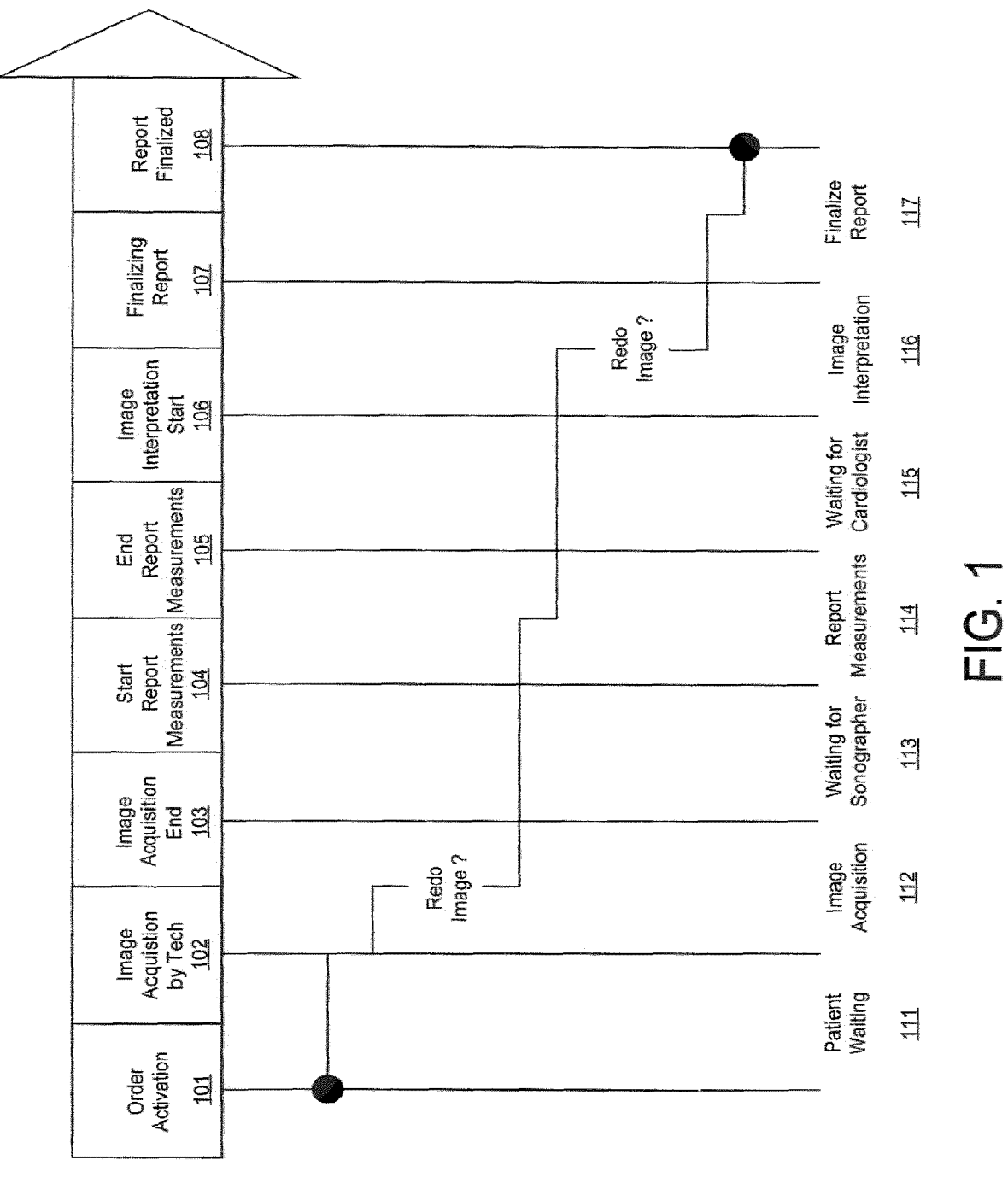
FIG. 1 is a process flow for an echo lab with image interpretation events.

FIG. 1 illustrates the events for an echocardiogram (echo) workflow. As will be understood by persons skilled in the art, the illustrated events are interrelated, and affect the turn-around time (TOT) for echo reports. The TOT is elapsed time between the order activated event 101 and the report finalization event 108. Between the order activation event 101 and the report finalization event 108, the following events occur in order: image acquisition start event 102, image acquisition end event 103, reporting measurements start event 104, reporting measurements end event 105, image interpretation start event 106, and image interpretation end event 107.

Between the order activation event 101 and the image acquisition start event 102, the process step patient waiting process step 111 takes place. Between the image acquisition start event 102 and the image acquisition end event 103, the process step image acquisition 112 is performed by the image acquisition technician. Between the image acquisition end event 103 and the reporting measurements start event 104, the waiting for sonographer process step 113 takes place. Between the reporting measurements start event 104 and the reporting measurements end event 105, the report measurements process step 114 is performed by the sonographer. Between the reporting measurement end event 105 and the image interpretation start event 106, the waiting for cardiologist process step 115 takes place. Between the image interpretation start event 106 and the image interpretation end event 107, the cardiologist performs the image interpretation process step 116. Between the image interpretation end event 107 and the report finalization event, the finalizing report process step 117 takes place.

Figure 2:
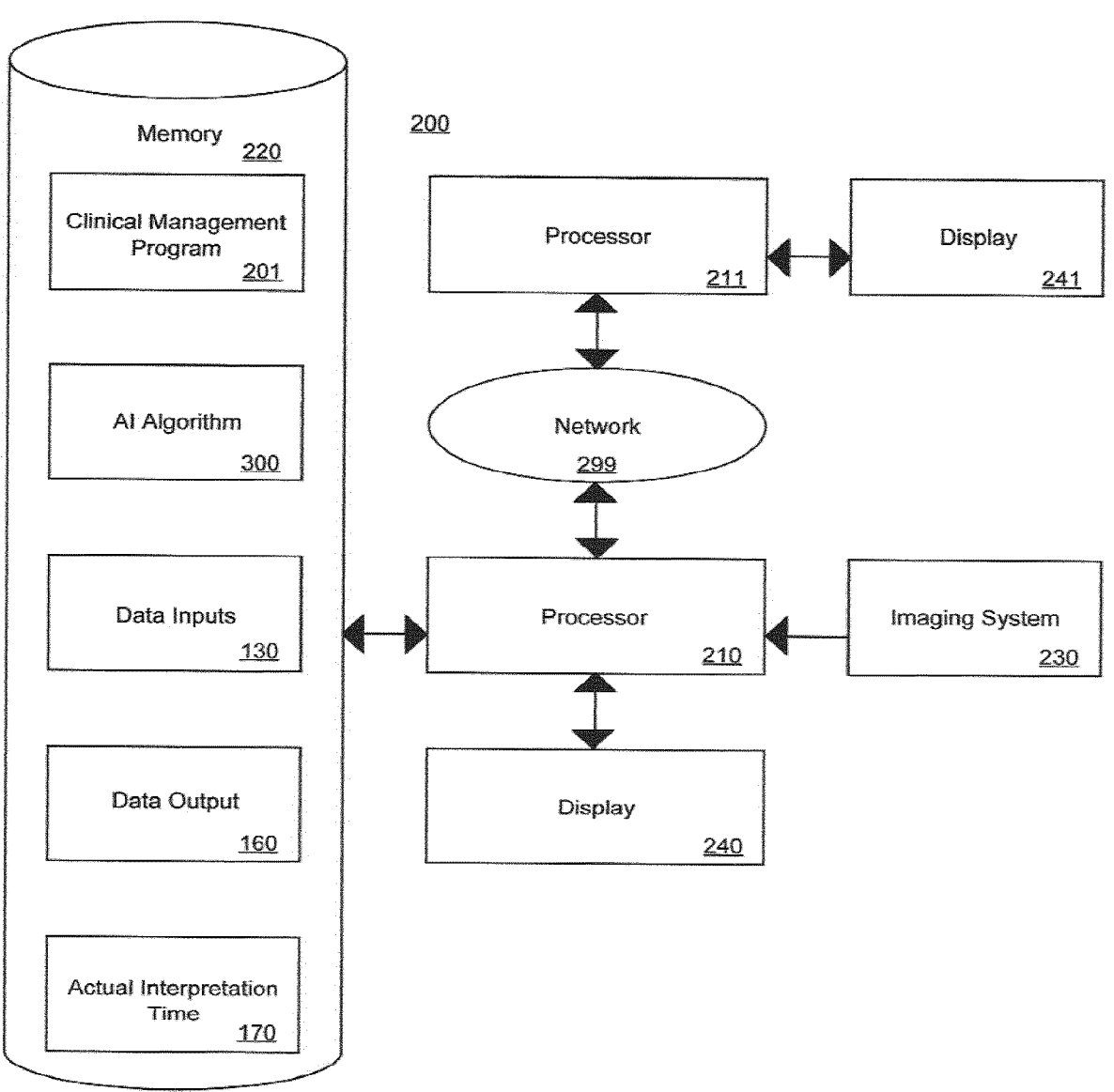
FIG. 2 is a block diagram of a clinical management system incorporating image interpretation time prediction according to an embodiment of the invention.

Each event is time-stamped by the clinical management system 200, shown in FIG. 2. Various types of data input 130 are provided through the clinical management system 200 from various sources and at different events in the echo workflow. One type of data that is available is clinical patient data, such as: patient age 131, patient gender 132, and patient body mass index (BMI) 133). Another type of data that may be available is patient medical history, such as: previous image modalities available 141, disease type 142, history of diastolic dysfunction 143, presence of atrial fibrillation (AF) 144, and presence of coronary artery disease (CAD) 145). Yet another type of data that is available is imaging examination data, such as: type of imaging modality 151, number of archived digital imaging communication in medicine (DICOM) images or loops 152, sonographer's notes 153, and exam type (representing exam complexity and number of measurements) 154, 155.

Clinical Management Systems, such as ISCV are designed to make a broad range of clinical patient data and patient history readily available to medical professionals to aid in efficient and accurate echo workflow. The clinical patient data 131, 132, 133 and patient medical history 141, 142, 143, 144, 145 may be provided at the order activation event 101 through the clinical management system 200. Various imaging examination data 151, 152, 153, 154, 155 may be provided at the order activation event 101 when it is already in the clinical management system 200, such as type of imaging modality 151 or at the reporting measurements end event 105, when it becomes available after the report measurement process step 114, such as sonographer's notes 153.

In this invention, a regression-based, artificial intelligence algorithm 300 uses the plurality of data inputs 130 (i.e., 131, 132, 133, 141, 142, 143, 144, 145, 151, 152, 153, 154, 155), and applies the algorithm to determine a predicted image examination interpretation time 161. While in one embodiment, each data input is used, in alternate embodiments various subsets of the data points may be used by the algorithm 300 to predict the image examination interpretation time. Also, embodiments are contemplated in which other data inputs may be used for interpreting different disease types or different imaging modalities.

BMI is one of the main factors affecting the complexity of echocardiogram image interpretation complexity, since image quality and complexity of tasks such as segmentation for volume measurements are adversely affected by high BMI. Thus, patient BMI 133 is an important data point for accurate prediction of image interpretation time.

Based on the American Society of echocardiography guidelines, it has been shown that age significantly affects the interpretation of diastolic parameters, including: mitral inflow velocity at early diastole (E), mitral inflow velocity at late diastole (A), and the ratio of mitral inflow velocity at early diastole to mitral inflow velocity at late diastole (E/A). Therefore, age 131 is a clinical patient data point significantly affecting image interpretation complexity, and therefore interpretation time.

It has been shown gender differences in terms of cardiac anatomy, remodeling and response to injuries which could lead to different image complexity and interpretation time.

Additionally, it has been shown that evaluation of A and E/A is challenging in AF patients, and E is challenging in patients with a history of CAD. Therefore, the presence of AF 144 and history of CAD 145 are patient medical history data points significantly affecting image interpretation complexity, and therefore interpretation time.

Previous imaging modalities available 141 may affect interpretation time, because the previous imaging modality images require time to review. Previous imaging modalities available will especially affect interpretation time if any inconsistencies exist between the ultrasound images to be interpreted and the previous imaging modality images require time to resolve. For example, if there are different longitudinal strain values in ultrasound and previous magnetic resonance (MR) imaging.

The disease type 142, such as heart failure with preserved ejection fraction or reduced ejection fraction or valvular heart disease, may determine the quantities and types of images required as well as the complexity of interpreting the images, and thus affect interpretation time.

Patients with history of diastolic dysfunction may go through a full diastolic study (with more parameter measurements) in the follow up exams causing more complexity and longer interpretation time.

The exam type 154 (limited versus comprehensive) determines both the number and complexity of measurements to be taken. A comprehensive echocardiogram needs more quantitative measurements or parameters to be collected, such as diastolic parameters of: flow propagation velocity (Vp), E, and A, mitral annular velocity at early diastole (e'), mitral annular velocity at late diastole (a'), ejection fraction, volume, and global longitudinal strain. A limited examination, however, only collects the ejection fraction and volume data. The difference in the number of quantitative measurements significantly affects image interpretation time.

The type of ultrasound imaging modality 151 (i.e. B-mode, color, tissue doppler imaging (TDI), contrast, and M-mode) also affects interpretation time. Color mode parameters, such as Vp and spectral M-mode parameters in cardiac imaging may require more interpretation time than b-mode only, for example.

Sonographer's annotations 153 can help to classify the current examination into different classes in terms of complexity. For example, left atrium volume is difficult to measure, and would therefore adversely affect interpretation time.

The number of archived images/loops 152 can affect interpretation time because of the time required to view the archived images/loops.

Table 1 shows two real-life use cases with different interpretation complexity resulting in very different interpretation times. Use case 1 represents a suspected amyloidosis patient (one of the aetiologies for heart failure with preserved ejection fraction). Use case 2 represents a patient with mitral valve prolapse. The presence of high BMI, discrepancies between strain values in CMR and U/S, several DICOM images/loops, multiple diastolic parameters and different and complex modes of ultrasound imaging in use case 1 caused a substantial difference in interpretation time compared to use case 2.

|  | Use case 1: difficult interpretation | Use case 2; easier interpretation |
|---|---|---|
| BMI 133 | Patient with high BMI (>30) | Patient with normal BMI |
| History of diastolic dysfunction 143 | history of diastolic dysfunction | no history of diastolic dysfunction |
| Previous image modalities available 141 | Both radial and longitudinal strain measurements available | No other image modalities available |
| Previous image modalities available 141 | Discrepancies between the strain values in cardiovascular magnetic resonance (CMR) imaging and longitudinal strain in U/S | |
| Disease type 142 | Heart failure with preserved ejection fraction | Mitral valve prolapse |
| Exam type 154 | Comprehensive transthoracic echocardiogram (TTE) | Limited TTE, Patient with normal ejection fraction (5 minutes) |
| Number of images/loops 152 | Several archived DICOM images/loops (30-50 minutes) | |
| Type of Ultrasound image modalities 151 | Color + TDI, m-Mode | B-mode only |

-continued

|  | Use case 1: difficult interpretation | Use case 2; easier interpretation |
|---|---|---|
| Approximate interpretation time | 50 minutes | 5 minutes |

FIG. 2 shows a clinical management system 200 incorporating image examination interpretation time prediction according to an embodiment of the invention. In the exemplary embodiment that follows, the clinical management system 200 is an imaging workflow management system for use in managing cardiological ultrasound imaging examinations. The system comprises a processor 210 which executes program code to provide clinical management data in various formats and at various locations. The processor 210 is operably connected to a memory 220, which comprises a machine-readable media with program code and data stored thereon. Specifically, a clinical management program 201 for managing and presenting imaging workflow is stored on the memory 220.

An artificial intelligence algorithm 300 is also stored on the memory 220. While the clinical management program 201 and the artificial intelligence algorithm 300 are shown stored on the same memory 220, memory 220 may alternatively be more than one memory media, and the clinical management system 200 and the artificial intelligence algorithm 300 may be stored on separate storage media.

Data input 130 to the artificial intelligence algorithm and data output 160 from the artificial intelligence algorithm 300 may also be stored in memory 220. As with clinical management program 201 and the artificial intelligence program 300, the data input 130 and data output 160 may be stored on the same memory media as clinical management program 201 and the artificial intelligence program 300 and each other, or they may be stored on different memory media, or a combination of some on the same memory media, and some on separate memory media.

Actual image interpretation time 170 may also be stored on memory 220, either on the same memory media as the other data or a separate memory media. Actual image interpretation time may be obtained by measuring reporting events, such as how long the reporting screen is active or how long a user interface like a mouse is active on a cardiologist's workstation.

The processor 210 is also operably connected to a display 240 which provides a visual user interface for a user to view imaging workflow data, such as queues for one of the workflow process steps (e.g., waiting for cardiologist).

An imaging system 230 is operably connected to the processor 210 to provide imaging data such as images and/or loops of images to the processor 210 so that they can be made available to a sonographer and cardiologist for measurement and interpretation. While the imaging system 230 is shown as being directly connected to the processor 210, it should be understood that the imaging system 230 may also be connected to the processor through a network 299, or the imaging data may be stored on a removable memory media and the media may be connected to the processor through a USB port or the like. Moreover, while the invention is described using ultrasound imaging system as imaging system 230, other imaging systems such as a magnetic resonance imaging (MRI) system, a computed tomography (CT) imaging system, a positron emission tomography (PET) imaging system, or any other known imaging system may also be used to practice the invention.

One or more additional processors 211 and displays 241 may be provided (in the form of workstations, for example) and be operably connected to the processor 210, such as through a network 299 for use by sonographers and cardiologists for accessing medical images for measurements and interpretation.

Figure 3:
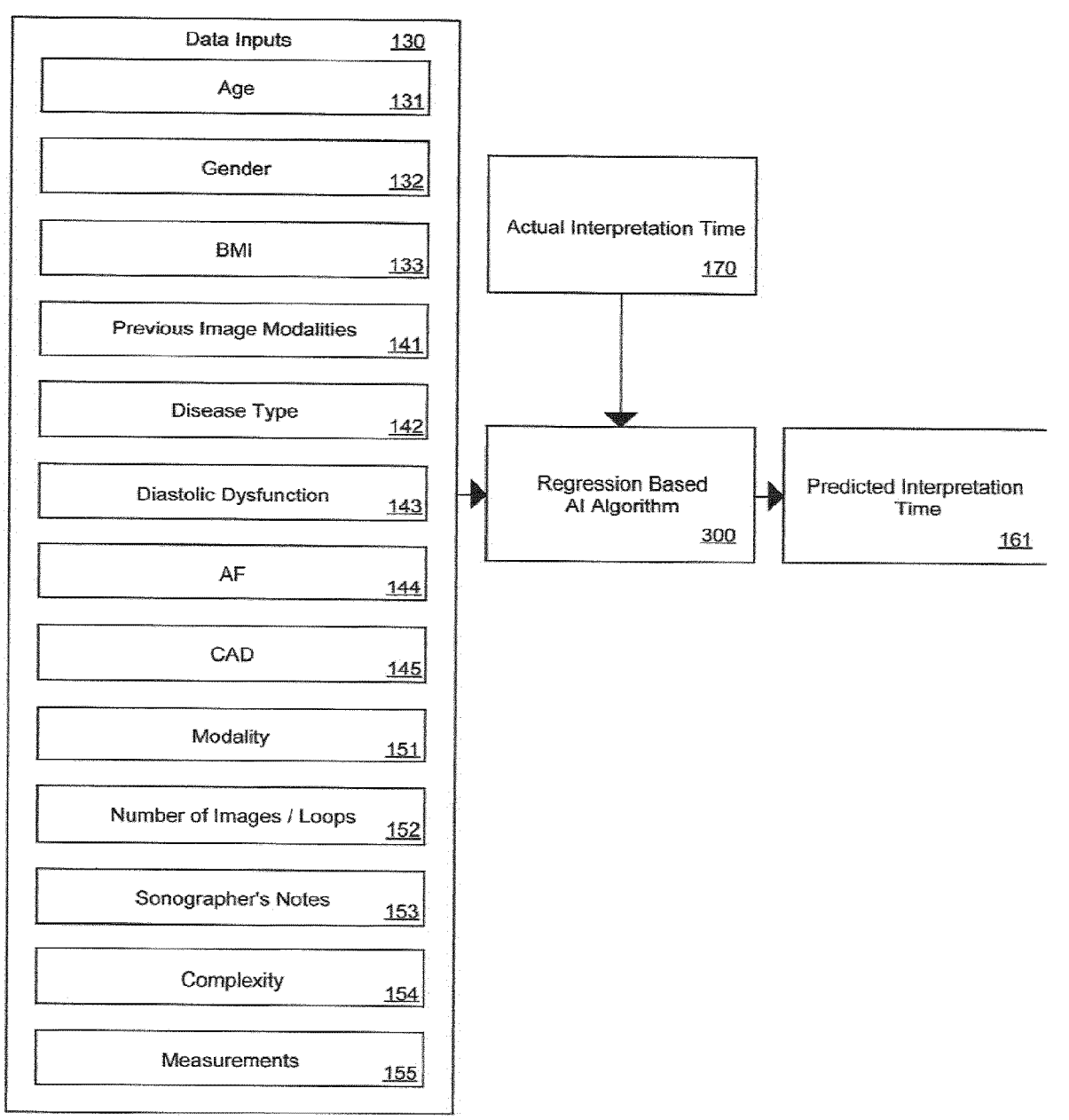
FIG. 3 is a process flow for a process for predicting image interpretation time according to an embodiment of the invention.

As shown in FIG. 3, data inputs 130, which may be obtained from the workflow management system 200, are provided to the Artificial intelligence algorithm 300. Alternatively, the data inputs 130 may be obtained from any of a plurality of healthcare information systems, such as electronic medical records, a radiology information system, a cardiology information system, or any combination of sources. These data inputs are highly heterogeneous, with different data types, data models, formats, and semantics. The AI algorithm 300 is responsible for interacting with different data sources to extract clinical and operational information associated with a clinical exam. The interfacing with clinical, operational, and demographic data sources can be done with any available state-of-the-art information technology communication protocol following specifications and standards such as Fast Hospital Interoperability Resources (FHIR), DICOM or the like.

As previously described, the data inputs 130 may include a combination of: patient age 131, patient gender 132, patient BMI 133), previous image modalities available 141, disease type 142, history of diastolic dysfunction 143, presence of AF 144, history of CAD 145, type of imaging modality 151, number of archived images or loops 152, sonographer's notes 153, and exam type 154.

The artificial intelligence algorithm 300 is a regression-based reinforcement learning (RL) algorithm. That means that the algorithm models dependencies and relationships between the target output and input features. In an exemplary embodiment, the regression-based AI algorithm 300 develops a mapping model. That is, it models the mapping of the data inputs 130 (variable attributes 131, 132, 133, 141, 142, 143, 144, 145, 151, 152, 153, 154, 155 which collectively define a state x) to a predicted interpretation time 161. Then the AI algorithm provides the predicted interpretation time 161 as data output 160. In addition to the estimated interpretation time, confidence (e.g. 95% CI) for the estimation can be provided in data output 160 to the clinical management system 200 to indicate to the user how likely the estimate is accurate. As will be described in more detail hereafter, the AI algorithm 300 uses reinforcement learning approach which uses trial and error to find a mapping model that optimizes a reward function r(x,a,j) where x is the initial state, a is the action or mapping, and j is the state resulting from action a.

Figure 6:
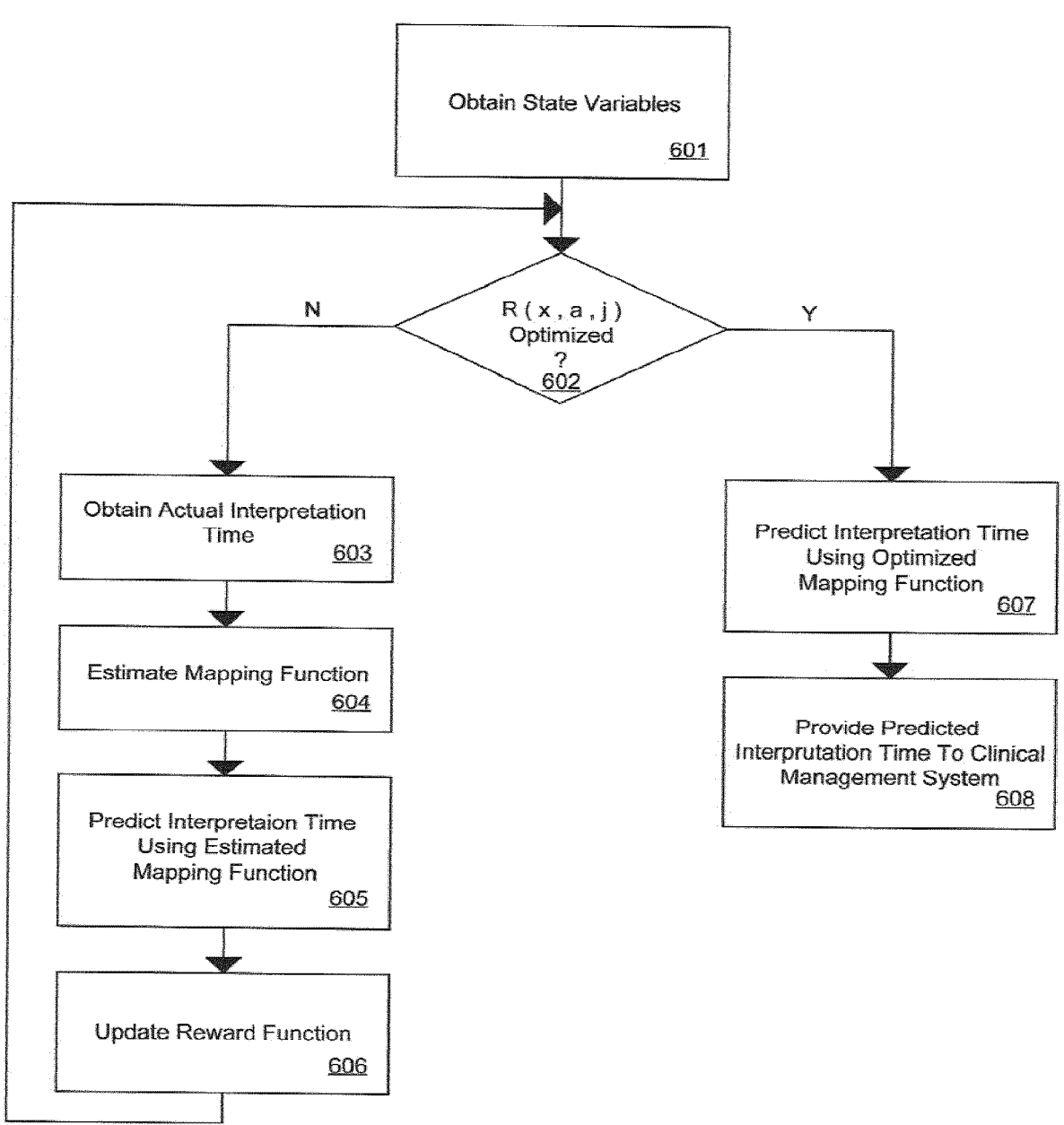
FIG. 6 is a flow diagram for a reinforcement learning network used in predicting image interpretation time according to an embodiment of the invention.

During a learning phase, illustrated in FIG. 6, the AI algorithm 300 uses a reinforcement learning approach to optimize itself such that it minimizes a reward function r(x,a,j). A reinforcement approach uses data input as state variables. The state variables $X=(x_1, x_2, x_3, x_4, x_5 \ldots)\epsilon X$ for interpretation time use all of the data inputs 131, 132, 133, 141, 142, 143, 144, 145, 151, 152, 153, 154, 155, where $x_1$ is age 131, $x_2$, is gender, $x_3$ is BMI, and so on. The output of the learning phase is the reward function r(x,a,j). According to one embodiment, the reward function r(x,a,j) is equal to the absolute value of the difference between the actual interpretation time and the predicted interpretation time multiplied by a disease type score.

$$R(x,a,j)=|\text{actual interpretation time–predicted interpretation time}|*\text{disease type score}$$

The disease type score gives more weight to the accuracy of the predicted interpretation time for disease types with more complex image interpretations (e.g., more images, more difficult views to interpret, more measurements required, etc.).

During the learning phase, data inputs 131, 132, 133, 141, 142, 143, 144, 145, 151, 152, 153, 154, 155 and actual interpretation times 171 collected from a plurality of exams are provided to the algorithm 300. The algorithm 300 sequentially predicts the interpretation time for each exam, then applies an optimization policy of minimizing the reward function r(x,a,j) to adjust the mapping model, thereby improving its predictions over time.

After the training phase, the AI algorithm 300 continues to provide a prediction time 161 as output 160 for each new exam to the clinical management system 200. The clinical management system 200 presents the predicted interpretation times to users, such as cardiologists, to help the users to manage the imaging workflow.

Depending on the clinical management platform (such as ISCV, web interface) that a cardiologist is using, the cardiologist may view a queue or list of pending (or unread) imaging examinations on the cardiologist's display 241. The AI algorithm 300 for predicting interpretation time can be incorporated in the workflow management system 200 as shown in FIG. 2. The predicted interpretation times may be presented for a queue of pending cases sorted in a variety of ways. Two ways of presenting pending cases are illustrated in FIGS. 4 and 5. In FIG. 4, pending cases are sorted by patient, showing predicted interpretation times for each patient to a cardiologist. In FIG. 5, pending cases are sorted by disease type, showing predicted interpretation times for each pending case to a cardiologist. Other formats for presenting pending cases with predicted interpretation times are also possible within the scope of the invention. In one embodiment the longest predicted interpretation times (e.g., one to three longest predicted interpretation times) and/or the shortest predicted interpretation times may be highlighted, such as by color-coding those longest and/or shortest cases (i.e. displaying the longest and/or shortest cases in different colors.

Figure 8:
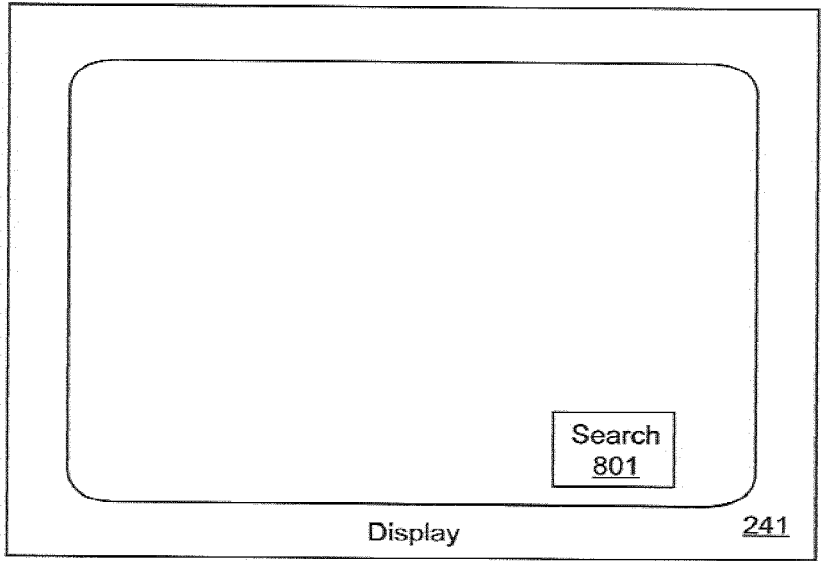
FIG. 8 shows a cardiologist's display with a search button for triggering the process of FIG. 7.

In one embodiment, a search button 801 (shown in FIG. 8) is provided to allow the user to view and compare predicted interpretation time of specific imaging types (e.g., strain imaging vs. color doppler) to facilitate imaging type decisions and planning prior to ordering an imaging examination.

The search button 801 triggers the trained AI algorithm 300 to predict an interpretation time for each of the imaging types using the mapping function and the state variable X. As the examination will not have been ordered and the images will not have been taken, some of the state variables may be estimates. The predicted interpretation times 161 for each selected imaging type is provided as output 160 to the clinical management system for presentation to a user (such as a cardiologist).

Figure 7:
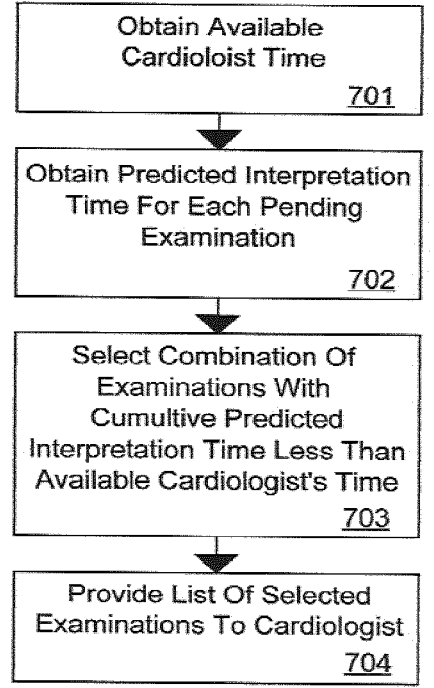
FIG. 7 is a flow diagram of a process for predicting image examination interpretation times for a plurality of examinations and recommending an examination plan based at least in part on the predicted image examination interpretation times according to an alternate embodiment of the invention.

FIG. 7 is a flow diagram for an alternate embodiment of the present invention. In this embodiment, a cardiologist provides a total reading time to the clinical management system 200 indicating the time that the cardiologist will be available to interpret that the cardiologist has available to interpret examination images. The clinical management system also obtains the predicted interpretation time 161 for each examination waiting for interpretation from the AI algorithm 300. Based on the total reading time, predicted interpretation times for each pending examination, and other filters (such as time remaining before breaching a service level agreement), the clinical management system 200 selects a combination of examinations to recommend to the cardiologist wherein the cumulative predicted interpretation times for the suggested examinations do not exceed the cardiologist's available reading time. Then, the clinical management system 200 provides the list of suggested examinations that can be read in the total reading time that is provided to the cardiologist.

As shown in FIG. 7, the workflow management system 200 obtains the cardiologist's available time (step 701). The cardiologist's available time may be obtained by response to a query on the cardiologist's display 241 and a cardiologist entering a response through a keyboard or other user interface.

The workflow management system 200 also obtains the predicted interpretation time for each examination that is waiting for interpretation (pending examinations) (step 702). Then, applying filters and prioritization (such as oldest pending examination first or longest examination first, or closest expected TOT (time since order plus predicted interpretation time) to service level agreement), the workflow management system 200 selects a combination of pending examinations with cumulative predicted interpretation times less than the cardiologist's available time (step 703) and provides a list of the selected examinations to the cardiologist (step 704). The list of selected examinations may be in the form of highlighted selected examinations on a list of all pending examinations or may be a stand-alone listing, or the selected examinations may be in any other form to reasonably inform the cardiologist of a recommended group of examinations that fit within the cardiologist's available time for interpretation.

Returning to FIG. 6, a process flow for the AI algorithm 300 begins by obtaining state variables X for a current examination or use case (step 601). As previously discussed, during the learning phase of the AI algorithm, the state variables may be for one of a plurality of archived use cases (examinations). The AI algorithm determines whether or not the mapping function has been optimized (step 602). This may be accomplished by a user input, for example, indicating that the AI algorithm is in a learning phase (not optimized) or a prediction phase (optimized). Alternatively, the optimization may be determined by the AI algorithm, based on convergence of the predicted interpretation time and actual interpretation time.

During the training phase, the actual interpretation time 170 is also obtained (step 603). Then, the AI algorithm estimates a mapping function from state variables X to a predicted interpretation time (step 604). The initial estimate may be a random approximation, with each successive estimation being a refinement based on a reward function feedback.

The AI algorithm uses the latest mapping function estimate to provide a predicted interpretation time 161 (step 605). As will be understood by those skilled in the art, the mapping function may be broken into smaller mapping steps during the training phase, and the estimated interpretation time 161 and the actual interpretation time 170 may then be used to update the reward function r(x,a,j) using a Bellman's equation for reinforcement learning (step 606). Then steps 603, 604, 605, and 606 are repeated until the reward function r(x,a,j) is minimized. The AI algorithm then uses the optimized mapping function to predict image interpretation time for a current exam (step 607) providing the predicted interpretation time 161 to the clinical management system 200 as output data 160 (step 608).

After the reward function r(x,a,j) is optimized, the optimized mapping function can be used to predict interpretation time 161 based on the obtained state variables X without using the actual interpretation time or the reward function. Alternatively, the AI algorithm 300 can continue to obtain the actual interpretation time 170 and continue to refine the mapping function to account for evolving interpretation techniques and performance within the institution.

While the invention is described with reference to echocardiographic imaging interpreted by cardiologist, the invention is not limited to this embodiment, but rather encompasses other types of medical imaging, such as magnetic resonance imaging (MRI), computed tomography (CT), positron emission tomography (PET), or any other known imaging type. Moreover, in addition to cardiologists medical imaging examination may be interpreted by radiologists, oncologists, orthopedic doctors, and other medical professionals. The state variables affecting interpretation times may also be different for different types of medical imaging and disease types.

The preceding description and accompanying drawing are intended to be illustrative and not limiting of the invention. The scope of the invention is intended to encompass equivalent variations and configurations to the full extent of the following claims.

101 order activation event
    102 image acquisition start event
    103 image acquisition end event
    104 reporting measurements start event
    105 reporting measurements end event
    106 image interpretation start event
    107 image interpretation end event
    108 report finalization event
    111 patient waiting process step
    112 image acquisition process step
    113 waiting for sonographer process step
    114 report measurements process step
    115 waiting for cardiologist process step
    116 image interpretation process step
    117 finalize report process step
    130 data input
    131 patient's age
    132 patient's gender
    133 patient's body mass index
    141 previous imaging modalities
    142 disease type
    143 diastolic dysfunction
    144 presence of atrial fibrillation
    145 history of coronary artery disease
    151 imaging modality
    152 number of images/loops
    153 sonographer's notes
    154 complexity of imaging
    160 data output
    161 predicted interpretation time
    170 actual interpretation time
    200 clinical management system
    201 clinical management program
    210 processor
    211 cardiologist's processor
    220 memory
    230 imaging system
    240 display
    241 cardiologist's display
    299 network
    300 AI algorithm
    401 image showing predicted interpretation time

501 alternate image showing predicted interpretation time
601 obtain state variables
602 determine whether or not the reward function is optimized
603 obtain actual interpretation time
604 estimate mapping function
605 predict interpretation time using estimated mapping function
606 update reward function
607 predict interpretation time using optimized mapping function
608 provide predicted interpretation time to clinical management system
701 obtain available cardiologist time
702 obtain predicted interpretation time for each pending examination
703 select combination of examinations with cumulative predicted interpretation time less than available cardiologist time
704 provide list of selected examinations to cardiologist
801 search button

What is claimed is:

1. A method implemented by a processor for optimizing prediction of interpretation times for a plurality of medical image examinations of subjects, each medical image examination comprising one or more medical images, the method comprising:

training a regression-based, artificial intelligence algorithm by obtaining training data inputs and corresponding actual interpretation times for a plurality of examinations, training the artificial intelligence algorithm to map states defined by the training data inputs to corresponding predicted interpretation times using a reinforcement learning approach, and minimizing a reward function to optimize the artificial intelligence algorithm to improve the predicted interpretation times over time, wherein the reward function comprises an absolute value of a difference between the predicted interpretation time and a corresponding actual interpretation time for each examination;

obtaining a plurality of data inputs associated with each medical image examination and/or each subject of said medical image examination, wherein data points of the plurality of data inputs represent examination variables affecting interpretation time;

inputting the plurality of data inputs associated with the medical image examinations and/or the subjects, respectively, to the trained artificial intelligence algorithm;

estimating corresponding optimized predicted interpretation times using the trained artificial intelligence algorithm based on said plurality of data inputs;

providing said predicted interpretation times to a user of a clinical management system performing interpretations of the medical image examinations;

obtaining available time of the user for image interpretation;

selecting a combination of medical image examinations waiting for interpretation having a cumulative predicted interpretation time less than the user's available time; and presenting a list of the selected combination of medical image examinations to the user for the user to perform the interpretations of the medical image examinations.

2. The method of claim 1, wherein the artificial intelligence algorithm further provides a confidence level for each of the predicted interpretation times.

3. The method of claim 1, wherein the artificial intelligence algorithm ranks the predicted interpretation times for the medical image examinations and highlights a longest predicted interpretation time.

4. The method of claim 1, wherein the plurality of data inputs comprises: at least one of body mass index of the subject of the medical image examination, patient age, or patient gender, at least one of type of medical image study, previous image modalities available, disease type, history of diastolic dysfunction, presence of atrial fibrillation, or presence of coronary artery disease, and at least one of type of imaging modality, number of archived images or loops, or exam type.

5. The method of claim 1, wherein the plurality of data inputs comprises each of: body mass index of the subject of the medical image examination, type of medical image study, patient age, patient gender, previous image modalities available, disease type, history of diastolic dysfunction, presence of atrial fibrillation, presence of coronary artery disease, type of imaging modality, number of archived images or loops, sonographer's notes, and exam type.

6. The method of claim 1, wherein the reward function is updated using a Bellman's equation for reinforcement learning.

7. The method of claim 1, further comprising:

obtaining actual interpretation time for each medical image examination, wherein the artificial intelligence algorithm uses the actual interpretation time and the plurality of data inputs for reinforcement learning by further minimizing the reward function to further optimize the artificial intelligence algorithm.

8. The method of claim 1, further comprising:

providing a search function to the user that triggers the artificial intelligence algorithm to predict an interpretation time for two or more selected imaging types using a mapping function and state variables X.

9. A clinical management system configured to optimize prediction of interpretation times for medical image examinations of subjects, the clinical management system comprising a processor operably connected to a non-transitory memory, the memory having encoded thereon machine-readable program code that, when executed by the processor, causes the processor to:

train a regression-based, artificial intelligence algorithm by obtaining training data inputs and corresponding actual interpretation times for a plurality of examinations, training the artificial intelligence algorithm to map states defined by the training data inputs to corresponding predicted interpretation times using a reinforcement learning approach, and minimizing a reward function to optimize the artificial intelligence algorithm to improve the predicted interpretation times over time, wherein the reward function comprises an absolute value of a difference between the predicted interpretation time and a corresponding actual interpretation time for each examination;

obtain a plurality of data inputs associated with each medical image examination and/or each subject of said medical image examination;

input the plurality of data inputs associated with the medical image examinations and/or the subjects, respectively, to the trained artificial intelligence algorithm;

estimate optimized predicted interpretation times using the trained artificial intelligence algorithm based on said plurality of data inputs;

display said predicted interpretation times to a user of the clinical management system performing interpretations of the medical image examinations;

obtain available time of the user for image interpretation;

select a combination of medical image examinations waiting for interpretation having a cumulative predicted interpretation time less than the user's available time; and present a list of the selected combination of medical image examinations to the user for the user to perform the interpretations of the medical image examinations.

10. The clinical management system of claim 9, wherein the predicted interpretation times are presented in a table of medical imaging examinations awaiting interpretation.

11. The clinical management system of claim 9, wherein the machine-readable program code, when executed by the processor, further causes the processor to:

provide a search function to the user that triggers the artificial intelligence algorithm to predict an interpretation time for two or more selected imaging types using a mapping function and state variables X.

12. The clinical management system of claim 9, wherein the artificial intelligence algorithm further automatically provides confidence levels for the predicted interpretation times, respectively, and the machine-readable program code, when executed by the processor, further causes the processor to:

provide said confidence levels to the user of the clinical management system performing interpretations of the medical image examinations.

13. A machine-readable storage media having encoded thereon program code for optimizing prediction of medical imaging interpretation time that, when executed by a processor, causes the processor to:

train a regression-based, artificial intelligence algorithm by obtaining training data inputs and corresponding actual interpretation times for a plurality of examinations, training the artificial intelligence algorithm to map states defined by the training data inputs to corresponding predicted interpretation times using a reinforcement learning approach, and minimizing a reward function to optimize the artificial intelligence algorithm to improve the predicted interpretation times over time, wherein the reward function comprises an absolute value of a difference between the predicted interpretation time and a corresponding actual interpretation time for each examination;

obtain a plurality of data inputs associated with each medical image examination and/or each subject of said medical image examination, wherein data points of the plurality of data inputs represent parameters affecting interpretation time;

input the plurality of data inputs associated with the medical image examinations and/or the subjects, respectively, to the trained artificial intelligence algorithm;

estimate corresponding optimized predicted interpretation times using the trained artificial intelligence algorithm based on said plurality of data inputs;

cause said predicted interpretation times to be displayed to a user of a clinical management system performing interpretations of the medical image examinations;

obtain available time of the user for image interpretation;

select a combination of medical image examinations waiting for interpretation having a cumulative predicted interpretation time less than the user's available time; and present a list of the selected combination of medical image examinations to the user for the user to perform the interpretations of the medical image examinations.

14. The machine-readable storage media of claim 13, wherein the artificial intelligence algorithm further provides confidence levels for the predicted interpretation times, respectively.

15. The machine-readable storage media of claim 13, wherein the artificial intelligence algorithm ranks the predicted interpretation times for medical image examinations and highlights a longest predicted interpretation time.

16. The machine-readable storage media of claim 13, wherein the plurality of data inputs comprises: at least one of body mass index of the subject of the medical image examination, patient age, or patient gender, at least one of type of medical image study, previous image modalities available, disease type, history of diastolic dysfunction, presence of atrial fibrillation, or presence of coronary artery disease, and at least one of type of imaging modality, number of archived images or loops, or exam type.

17. The machine-readable storage media of claim 13, wherein the plurality of data inputs comprises each of: body mass index of the subject of the medical image examination, type of medical image study, patient age, patient gender, previous image modalities available, disease type, history of diastolic dysfunction, presence of atrial fibrillation, presence of coronary artery disease, type of imaging modality, number of archived images or loops, sonographer's notes, and exam type.

* * * * *